United States Patent
Kim et al.

(10) Patent No.: US 9,206,132 B2
(45) Date of Patent: Dec. 8, 2015

(54) USE OF A NOVEL AMINOPYRIDINE DERIVATIVE TO PREVENT OR TREAT CANCER

(71) Applicant: Medicinal Bioconvergence Research Center, Suwon-si (KR)

(72) Inventors: Sunghoon Kim, Seoul (KR); Hee Sook Lee, Seoul (KR); Young Sun Oh, Seoul (KR); Dae Gyu Kim, Seoul (KR)

(73) Assignee: Medicinal Bioconvergence Research Center, Suwon-si (KR)

( * ) Notice: Subject to any disclaimer, the term of this patent is extended or adjusted under 35 U.S.C. 154(b) by 0 days.

(21) Appl. No.: 14/518,753

(22) Filed: Oct. 20, 2014

(65) Prior Publication Data
US 2015/0038531 A1     Feb. 5, 2015

Related U.S. Application Data

(63) Continuation of application No. PCT/KR2013/003347, filed on Apr. 19, 2013.

(30) Foreign Application Priority Data

Apr. 20, 2012 (KR) ........................ 10-2012-0041623

(51) Int. Cl.
C07D 213/75 (2006.01)
A61K 31/435 (2006.01)
C07D 215/38 (2006.01)

(52) U.S. Cl.
CPC ............ *C07D 215/38* (2013.01); *A61K 31/435* (2013.01); *C07D 213/75* (2013.01)

(58) Field of Classification Search
None
See application file for complete search history.

(56) References Cited

U.S. PATENT DOCUMENTS

2009/0163545 A1    6/2009    Goldfarb

FOREIGN PATENT DOCUMENTS

| KR | 10-0575251 | 5/2006 |
|---|---|---|
| KR | 10-0762995 | 10/2007 |
| WO | 2007/044724 | 4/2007 |
| WO | 2010/151791 | 12/2010 |
| WO | WO 2011/095196 A1 * | 8/2011 |

OTHER PUBLICATIONS

Choi, et al., "Cancer-Associated Splicing Variant of Tumor Suppressor AIMP2/p38: Pathological Implication in Tumorigenesis," PLOS Genetics, Mar. 31, 2011, pp. 1-13, vol. 7, Issue 3.

Collins, "Generation and Initial Analysis of More than 15,000 Full-Length Human and Mouse cDNA Sequences," PNAS, Dec. 24, 2002, pp. 16899-16903, vol. 99, No. 26.

Han, et al., "AIMP2/p38, the Scaffold for the Multi-tRNA Synthetase Complex, Responds to Genotoxic Stresses Via p53," PNAS, Aug. 12, 2008, pp. 11206-11211, vol. 105, No. 32.

Kim, et al., "Downregulation of Fuse-binding protein and c-myc by tRNA synthetase cofactor p38 is required for lung cell differentiation," Nature Genetics, Jul. 3, 2003, pp. 330-336, vol. 34, No. 3, Natuare Publishing Group.

Mekheimer, et al., "Synthesis of Some Novel Azido- and tetrazoloquinoline-3-carbonitriles and their conversion into 2,4-diaminoquinoline-3-carbonitriles," Journal of Chemical Research, Feb. 2005, pp. 82-85.

* cited by examiner

*Primary Examiner* — Zinna Northington Davis
(74) *Attorney, Agent, or Firm* — H.C. Park & Associates, PLC

(57) ABSTRACT

An aminopyridine derivative of Formula 1 and a method of preventing or treating cancer using the same. Formula 1:

[Formula 1]

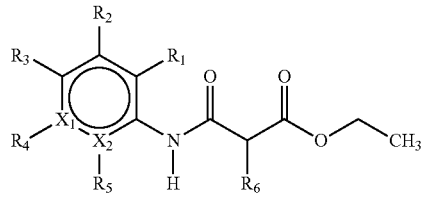

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6.

5 Claims, 2 Drawing Sheets

USE OF A NOVEL AMINOPYRIDINE DERIVATIVE TO PREVENT OR TREAT CANCER

CROSS REFERENCE TO RELATED APPLICATIONS

This application is a continuation of International Application No. PCT/KR2013/003347, filed on Apr. 19, 2013, and claims priority from and the benefit of Korean Patent Application No. 10-2012-0041623, filed on Apr. 20, 2012, all of which are incorporated herein by reference in its entirety for all purposes as if fully set forth herein.

BACKGROUND

1. Field

Exemplary embodiments of the present invention relates to the use of novel aminopyridine derivatives to prevent or treat cancer, and more particularly to novel aminopyridine derivatives or pharmaceutically acceptable salts thereof, and a pharmaceutical composition for preventing or treating cancer comprising the same.

2. Discussion of the Background

It has been shown by molecular and cell biological analyses that the expression of AIMP2 (ARS-interacting multifunctional protein 2) is induced by TGF-β and AIMP2 proteins translocate to nucleus where they inhibit the expression of c-myc, whereas genetic disruption of AIMP2 induces the over-expression of c-myc, leading to the hyperproliferation of alveolar epithelial cells of the lung which causes neonatal lethality (M. J. Kim, B.-J. Park, Y.-S. Kang, H. J. Kim, J.-H. Park, J. W. Kang, S. W. Lee, J. M. Han, H.-W. Lee, S. Kim, Nat. Genet. 34, 330-336, 2003).

Korean Patent Application No. 2005-110946 discloses that AIMP2 is a novel tumor suppressor with a function of enhancing TGF-β by signaling through directly interaction with Smad2/3, and its exon2-deleted form of splicing variants, namely AIMP2DX2, is expressed specifically in cancer cell lines and tissues. In addition, it was confirmed that the levels of AIMP2 were dramatically reduced regardless of TGF-β in the cells transfected with AIMP2DX2, demonstrating that the production of AIMP2DX2 inactivates AIMP2. Since AIMP2DX2 downregulates AIMP2 and is closely associated with cancer formation or progression, it was demonstrated that various types of cancers (such as lung cancer, liver cancer, skin cancer, breast cancer, renal cell carcinoma, and osteosarcoma) can be diagnosed based on the expression of AIMP2. Korean Patent Application No. 2005-110946 in its entirety is hereby incorporated by reference.

Korean Patent Application No. 2005-110946 discloses that AIMP2 is a novel tumor suppressor with a function of enhancing TGF-β signaling through direct interaction with Smad2/3, and its exon2-deleted form of splicing variants, namely AIMP2DX2, is expressed specifically in cancer cell lines and tissues. In addition, it was confirmed that the levels of AIMP2 were dramatically reduced regardless of TGF-β in the cells transfected with AIMP2DX2, demonstrating that the production of AIMP2DX2 inactivates AIMP2. Since AIMP2DX2 downregulates AIMP2 and is closely associated with cancer formation or progression, it was demonstrated that various types of cancers (such as lung cancer, liver cancer, skin cancer, breast cancer, renal cell carcinoma, and osteosarcoma) can be diagnosed based on the expression of AIMP2. Korean Patent Application No. 2005-110946 in its entirety is hereby incorporated by reference.

The AIMP2DX2 protein is a splicing variant of AIMP2 in which the second exon is deleted from the AIMP2 protein sequence. Sequences of the AIMP2 protein (312 aa version: AAC50391.1 or GI: 1215669; 320 aa version: AAH13630.1, GI: 15489023, BC013630.1) are found in the literatures (312 aa version: Nicolaides, N. C., et. al., Genomics 29 (2), 329-334 (1995)/320 aa version: Generation and initial analysis of more than 15,000 full-length human and mouse cDNA sequences, Proc. Natl. Acad. Sci. U.S.A. 99 (26), 16899-16903 (2002)). Korean Patent Application No. 10-2003-0018424 discloses a cancer-treating effect of AIMP2 protein, and its description of AIMP2 protein is hereby incorporated by reference.

Moreover, AIMP2 facilitates apoptosis by activating p53 when DNA is damaged (Han J M, et. al., Proc Natl Acad Sci USA, 105: 11206-11211 (2008)). AIMP2-DX2 was found to cause cancer by compromising pro-apoptotic activity of AIMP2 through competitive binding to p53 and interruption of binding between AIMP2 and p53 (Choi J W, et al., PLOS GENETICS, 7(3):e1001351, 2011). Thus, the publication describes AIMP2-DX2 as a potential and novel target for anticancer agents.

The above information disclosed in this Background section is only for enhancement of understanding of the background of the inventive concept, and, therefore, it may contain information that does not form the prior art that is already known in this country to a person of ordinary skill in the art.

SUMMARY

Accordingly, the present inventors developed an anticancer agent capable of controlling cancerous cells specifically without causing cytotoxicity in healthy cells, wherein the anticancer agent down-regulates AIMP2-DX2 by degrading mRNA of AIMP2-DX2, thereby inhibiting cancer growth. The inventors discovered that the compounds defined by the following Formula 1 exhibit the above-mentioned effect and are useful as an anticancer agent. Such discoveries are associated with various exemplary embodiments disclosed herein. However, aspects of the present invention are not limited thereto.

An exemplary embodiment of the present invention provides an aminopyridine derivative represented by Formula 1 or a pharmaceutically acceptable salt thereof.

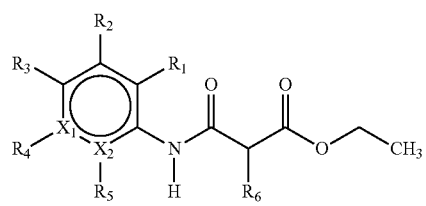

[Formula 1]

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6.

An exemplary embodiment of the present invention provides a pharmaceutical composition for treating or preventing cancer including an aminopyridine derivative represented by Formula 1 or pharmaceutically acceptable salt thereof.

[Formula 1]

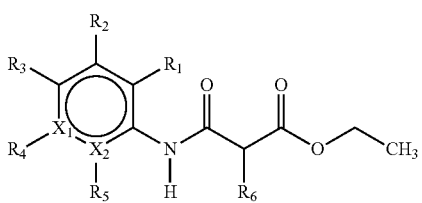

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6.

An exemplary embodiment of the present invention provides a use of aminopyridine derivative or a pharmaceutically acceptable salt thereof for preparing an agent for treating or preventing a cancer.

An exemplary embodiment of the present invention provides a method of treating or preventing cancer including administering an effective amount of an aminopyridine derivative or a pharmaceutically acceptable salt thereof to a subject in need thereof.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
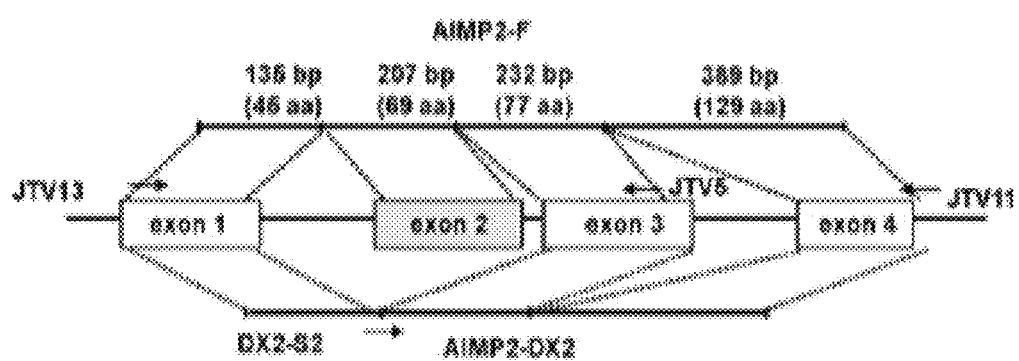
FIG. 1 shows a location map of primers used to examine the mechanisms by which the compounds suppress AIMP2-DX2 according to an exemplary embodiment of the present invention.

Hereinafter, exemplary embodiments of the present invention will be described in detail by examples. It is to be understood, however, that these examples are for illustrative purpose only and are not construed to limit the scope of the present invention.

In order to achieve various objects described above, an aminopyridine derivative represented by Formula 1 or a pharmaceutically acceptable salt thereof is provided.

[Formula 1]

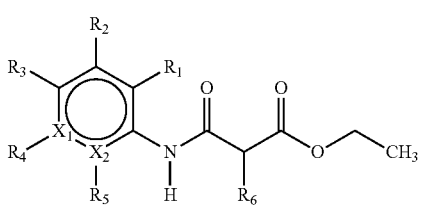

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6.

In addition, an exemplary embodiment of the present invention provides a pharmaceutical composition for treating or preventing a cancer including an aminopyridine derivative represented by Formula 1 or a pharmaceutically acceptable salt thereof as an active ingredient.

[Formula 1]

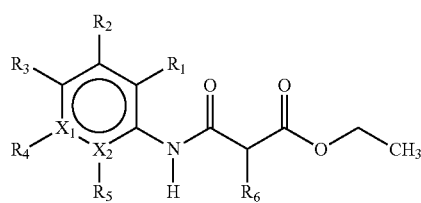

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6.

An exemplary embodiment of the present invention provides the use of the above described aminopyridine derivative or a pharmaceutically acceptable salt thereof for preparing an agent for treating or preventing a cancer.

Further, an exemplary embodiment of the present invention provides a method of treating or preventing a cancer including administering an effective amount of the above described aminopyridine derivative or a pharmaceutically acceptable salt thereof to a subject in need thereof.

Hereinafter, exemplary embodiments of the present invention will be described in detail.

[Formula 1]

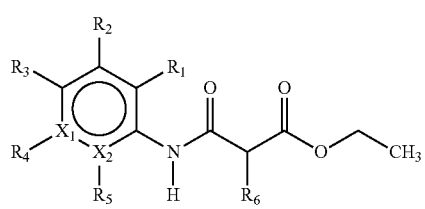

The compound according to an exemplary embodiment of the present invention is represented by Formula 1.

In Formula 1: X1 and X2 are each independently selected from the group consisting of carbon and nitrogen; R1 to R5 are each independently selected from the group consisting of a hydrogen, a straight, a branched, or cyclo alkyl of C1-C4, a halogen, and a hydroxyl; and R6 is a hydrogen or an alkyl of C1-C6. According to aspects, X1 and X2 may be different elements selected from carbon and nitrogen.

The term "alkyl" as used herein refers to a straight or branched saturated hydrocarbon radical, as long as it is not defined otherwise.

The term "halogen" or "halo" as used herein, refers to halogen atoms, and includes fluorine, chlorine, bromine, iodine, and the like.

The term "alkoxy" as used herein refers to O-alkoxy (alkyl is described above) as long as it is not defined otherwise.

The term "cycloalkyl" as used herein refers to saturated hydrocarbon ring as long as it is not defined otherwise.

More preferably, the compound represented by Formula 1 is selected from the group consisting of ethyl 3-[(5-chloropyridin-2-yl)amino]-2-methyl-3-oxopropanoate, ethyl 3-[(6-methylpyridin-2-yl)amino]-3-oxopropanoate, ethyl 3-oxo-3-(quinolin-3-ylamino)propanoate), ethyl 3-[(3,6-dimethylpyridin-2-yl)amino]-3-oxopropanoate, ethyl 3-[(4-hydroxypyridin-2-yl)amino]-3-oxopropanoate, ethyl 2-methyl-3-oxo-3-(quinolin-3-ylamino)propanoate, ethyl 2-methyl-3-[(6-methylpyridin-2-yl)amino]-3-oxopropanoate, ethyl 3-[(5-chloropyridin-2-yl)amino]-3-oxopropanoate.

The compound represented by Formula 1 includes a pharmaceutically acceptable salt thereof. The pharmaceutically acceptable salt includes an acid addition salt formed with an inorganic acid or organic acid. Specifically, the salt may be an acid addition salt formed from a pharmaceutically acceptable free acid. The free acid may be an organic or inorganic acid. For the inorganic acid, hydrochloric acid, bromic acid, sulfuric acid, phosphoric acid and the like may be used. For the organic acid, citric acid, acetic acid, lactic acid, tartaric acid, fumaric acid, formic acid, propionic acid, oxalic acid, trifluoroacetic acid, methanesulfonic acid, benzensulfonic acid, maleic acid, benzoic acid, gluconic acid, glycolic acid, succinic acid, 4-morpholinethansulfonic acid, cam-phorsulfonic acid, 4-nitrobenzenesulfonic acid, hydroxy-O-sulfonic acid, 4-toluenesulfonic acid, caloktronic acid, amber acid, glutamic acid, aspartic acid and the like may be used.

The compounds of Formula 1 showed the effect of promoting cell death and inhibiting cellular growth specifically in cancer cells by restoring the cellular level of AIMP2 to its normal level and thus strengthening the damaged tumor suppressive signal, TGFβ. Furthermore, the compound described herein can be particularly advantageous as a novel anticancer agent because it suppresses tumorigenesis and restores normal cell signaling pathways by targeting cancer-specific mechanisms, unlike conventional anticancer drugs which induce cell death based on nonspecific cytotoxicity.

In an example, compounds were screened for their capacity to downregulate AIMP2-DX2 in cancer cells. As a result, it was confirmed that 4-[(3-ethoxy-1,3-dioxopropyl)amino]-benzoic acid inhibited the activity of AIMP2-DX2 effectively in cancer cells.

In another example, various novel derivatives sharing the aminopyridine structure with 4-[(3-ethoxy-1,3-dioxopropyl)amino]-benzoic acid were synthesized and determined whether they could inhibit the activity of AIMP2-DX2. As a result, it was confirmed that the provided aminopyridine derivatives effectively reduced the activity of AIMP2-DX2 in cancer cells similar to 4-[(3-ethoxy-1,3-dioxopropyl)amino]-benzoic acid.

Accordingly, it was confirmed that aminopyridine derivatives in accordance with exemplary embodiments of the present invention effectively suppressed cancer cells.

Therefore, exemplary embodiments of the present invention provide a pharmaceutical composition for treating or preventing a cancer including the aminopyridine derivative represented by Formula 1 or a pharmaceutically acceptable salt thereof.

The composition in accordance with an exemplary embodiment of the present invention preferably refers to, but is not limited thereto, a pharmaceutical composition. As used herein, the term "pharmaceutically acceptable" means a composition which is physiologically acceptable and, when administered to human beings, generally does not cause allergic reactions, such as gastrointestinal disorders and dizziness, or similar reactions thereto, and does not inhibit reaction of an active ingredient. A pharmaceutically acceptable carrier includes, for example, a carrier for oral preparations such as lactose, starch, cellulose derivatives, magnesium stearate, stearic acid and a carrier for parenteral preparations such as water, suitable oil, saline, aqueous glucose and glycol, while it may further include a stabilizer and a preservative. The examples of the suitable stabilizer may be an antioxidant such as sodium hydrogen sulfite, sodium sulfite, and ascorbic acid. The examples of the preservatives may be benzalkonium chloride, methyl- or prophyl-paraben, and chlorobutanol. The list of pharmaceutically acceptable carriers is disclosed in Remington's Pharmaceutical Sciences, 19th ed., Mack Publishing Company, Easton, Pa., 1995. The pharmaceutical composition in accordance with an exemplary embodiment of the present invention may be prepared in various formulations for oral administration or parenteral administration according to various methods including methods well-known in the art. In case of parenteral administration, the composition may be formulated preferably into injections of isotonic solution or suspension. The injections may be prepared by various methods including methods well-known in the art with a proper dispersion agent, a wetting agent or a suspension agent. For example, each component may be dissolved into saline or buffer solution and formulated into injections. In addition, a formulation for oral administration may include, but is not limited thereto, powders, granules, tablets, pills and capsules.

The pharmaceutical composition prepared by the above may be administered by various routes including oral, transdermal, intradermal, intravenous, and intramuscular administrations. As used herein, "effective amount" refers to an amount of a compound or composition, which exhibits the effect of preventing or treating a disease when it is administered into the patient. The dose of the pharmaceutical composition may be suitably determined by considering various factors, such as administering route, subject, age, sex, differences among individuals, and disease severity. Preferably, the anticancer composition may contain variable amount of the effective ingredient according to the disease severity, but 0.0001 μg/kg to 10 g/kg of the effective ingredient in a single dose may be administered several times a day.

The anticancer composition in accordance with an exemplary embodiment of the present invention is very effective in treating a cancer. The cancer includes, but is not limited to, breast cancer, colorectal cancer, lung cancer, small cell lung cancer, stomach cancer, liver cancer, leukemia, bone cancer, pancreatic cancer, skin cancer, head or neck cancer, melanoma in skin or eyeball, uterine cancer, ovarian cancer, rectal cancer, anus cancer, colon cancer, oviduct cancer, endometrial carcinoma, cervical cancer, vagina cancer, vulva cancer, Hodgkin's disease, esophagus cancer, small intestine cancer, endocrine gland cancer, thyroid cancer, parathyroid cancer, adrenal gland cancer, soft tissue sarcoma, urethra cancer, penis cancer, testis cancer, prostate cancer, chronic or acute leukemia, lymphocyte lymphoma, bladder cancer, kidney or ureter cancer, kidney cell carcinoma, kidney pelvis carcinoma, CNS tumor, primary CNS lymphoma, spinal cord tumor, brainstem glioma, pituitary adenoma or combinations thereof. In particular, it may be lung cancer.

Exemplary embodiments of the present invention provide a use of an aminopyridine derivative or a pharmaceutically acceptable salt thereof for preparing an agent for preventing or treating a cancer.

Exemplary embodiments of the present invention provide a method of treating or preventing a cancer including administering an effective amount of the above described aminopyridine derivative or a pharmaceutically acceptable salt thereof to a subject in need thereof.

The above-mentioned cancer is characterized by one or more diseases selected from the group consisting of breast cancer, colorectal cancer, lung cancer, small cell lung cancer, stomach cancer, liver cancer, leukemia, bone cancer, pancreatic cancer, skin cancer, head or neck cancer, melanoma in skin or eyeball, uterine cancer, ovarian cancer, rectal cancer, anus cancer, colon cancer, oviduct cancer, endometrial carcinoma, cervical cancer, vagina cancer, vulva cancer, Hodgkin's disease, esophagus cancer, small intestine cancer, endocrine gland cancer, thyroid cancer, parathyroid cancer, adrenal gland cancer, soft tissue sarcoma, urethra cancer, testis cancer, penis cancer, prostate cancer, chronic or acute leukemia, lymphocyte lymphoma, bladder cancer, kidney or ureter cancer, kidney cell carcinoma, kidney pelvis carcinoma, CNS tumor, primary CNS lymphoma, spinal cord tumor, brainstem glioma, and pituitary adenoma.

The aminopyridine derivative or a pharmaceutically acceptable salt thereof may be administered by various routes including oral, transdermal, intradermal, intravenous, and intramuscular administrations. As used herein, "effective amount" refers to an amount which exhibits the effect of preventing or treating a cancer when it is administered into a patient. As used herein, "subject" may include an animal, preferably a mammal, particularly including a human, as well as cells, tissues, organs originated from animals. A subject may refer to a patient requiring medical treatments.

The aminopyridine derivative or a pharmaceutically acceptable salt thereof may be administered as it is or as various forms of formulation prepared as described above, preferably until the treatment results in the desired effect of treating or preventing a cancer. Compounds in accordance with exemplary embodiments of the present invention may be administered by various routes according to various methods including methods well known in the art, for example, oral or parenteral administration. The parenteral route includes, but is not limited thereto, for example, intramuscular, intravenous, intracutaneous, intraarterial, intraosseous, intrathecal, intraperitoneal, nasal, intravaginal, intrarectal, sublingual or subcutaneous administration or administration through the gastrointestinal tract, the mucosal membrane and the respiratory tract. For instance, the pharmaceutical composition according to exemplary embodiments of the present invention may be applied topically on the skin or prepared into an injectable formulation, and then administered by lightly pricking the skin with a 30 gauge thin injection needle. Alternatively, it may be directly applied to the skin of the subject. In addition, the aminopyridine derivative or a pharmaceutically acceptable salt thereof may be administered as attached to molecules evoking high-affinity binding to the target cells or tissues (for example, skin cells or tissues), or as capsulated within such molecules. The aminopyridine derivative or a pharmaceutically acceptable salt thereof may be coupled or cross-liked with sterols (for example, cholesterol), lipids (for example, cationic lipids, virosomes or liposomes) or target cell-specific bonding agents (for example, ligands recognized by target-cell specific receptors). Coupling agents or cross-linking agents include, but are not limited to, protein A, carbodiimide, N-succinimidyl-3-(2-pyridyldithio)propionate (SPDP).

These formulations are described in Remington's Pharmaceutical Sciences, 19th ed., Mack Publishing Company, Easton, Pa., 1995, which is the general reference well known in the pharmaceutical chemistry field.

Therefore, the compound of Formula 1 according to an exemplary embodiment of the present invention inhibits the activation of AIMP2-DX2 as a novel anticancer target, thereby effectively inducing cell death in cancer cells and thus effecting prevention and treatment of a cancer. Hence, the compound in accordance with an exemplary embodiment of the present invention can be used to prevent and treat a cancer.

EXAMPLE 1

Screening for Compounds which Possess an Inhibitory Effect on Lung Cancer

Figure 2:
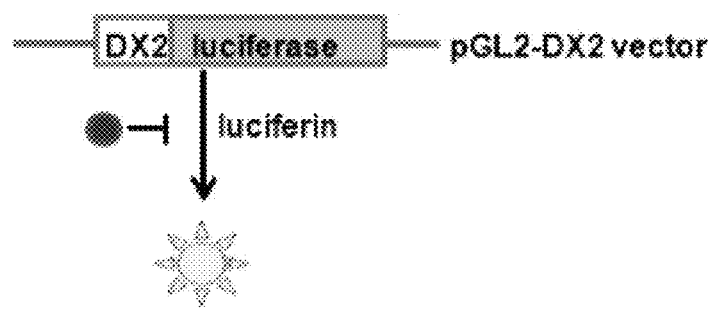
FIG. 2 shows a schematic map of DX2-luciferase vector (a vector modified to be expressed under the control of the AIMP2-DX2 promoter) transfected into the lung cancer cell lines for a luciferase assay according to an exemplary embodiment of the present invention.

In order to screen for compounds specifically inhibiting the activity of AIMP2-DX2 from a compound library purchased from ChemDive (US), the inventors transfected the lung cancer cell line, H460, with pGL2-DX2 (see FIG. 2). After 24 hours in culture, transfected lung cancer cells were treated with the compounds of the library. 4 hours later, luciferase activity was measured with a luminometer using a luciferase assay kit according to a manufacturer protocol (Promega, US).

As a result, 22 compounds were initially selected from the first screen and additionally tested for cytotoxicity. Normal cells, i.e. the WI-26 cell line were treated with each of the 22 compounds. 48 hours later, cytotoxicity of each compound was examined using a MTT assay. As a result, the following compound of Formula 2 was finally selected (data not shown).

[Formula 2]

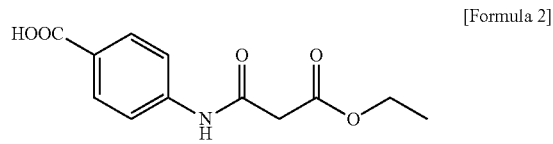 [SMILES: CCOC(=O)CC(=O)Nc1ccc(C(=O)O)cc1]

EXAMPLE 2

Inhibitory Effect of the Inventive Compounds on Lung Cancer

Novel aminopyridine derivatives having a similar structure as 4-[(3-ethoxy-1,3-dioxopropyl)amino]-benzoic acid were synthesized (see Tables 1 to 4), and their cancer-inhibiting effect was examined in the same manner as Example 1. Lung cancer cell lines A549 and H460 were transfected with pGL-DX-2, cultured for 24 hours, and treated with the newly synthesized compounds. After further culturing for 4 hours, luciferase activity was measured. Luciferase activity of a negative control group (N.C) and a positive control group (P.C), treated with DMSO instead of the inventive compounds and 4-[(3-ethoxy-1,3-dioxopropyl)amino]-benzoic acid, respectively, were measured as well.

As a result, as noted in Table 2, it was confirmed that the novel aminopyridine derivatives had an outstanding cancer-inhibiting effect similar to 4-[(3-ethoxy-1,3-dioxopropyl)amino]-benzoic acid.

TABLE 1

| No. | Chemical Structure | Name |
|---|---|---|
| 1 | 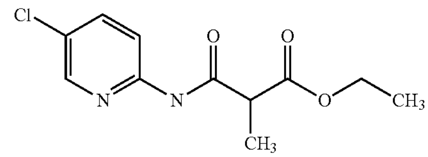 [SMILES: CCOC(=O)C(C)C(=O)Nc1ccc(Cl)cn1] | ethyl 3-[(5-chloropyridin-2-yl)amino]-2-methyl-3-oxopropanoate |
| 2 | 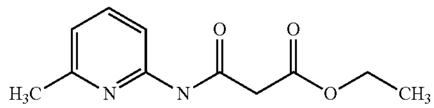 [SMILES: CCOC(=O)CC(=O)Nc1cccc(C)n1] | ethyl 3-[(6-methylpyridin-2-yl)amino]-3-oxopropanoate |
| 3 | 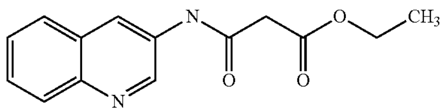 [SMILES: CCOC(=O)CC(=O)Nc1cnc2ccccc2c1] | ethyl 3-oxo-3-(quinolin-3-ylamino)propanoate) |
| 4 | 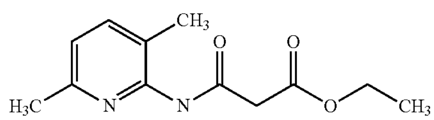 [SMILES: CCOC(=O)CC(=O)Nc1nc(C)ccc1C] | ethyl 3-[(3,6-dimethylpyridin-2-yl)amino]-3-oxopropanoate |
| 5 | 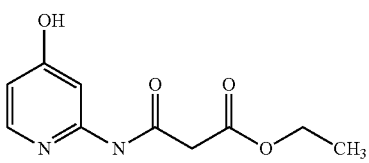 [SMILES: CCOC(=O)CC(=O)Nc1cc(O)ccn1] | ethyl 3-[(4-hydroxypyridin-2-yl)amino]-3-oxopropanoate |
| 6 | 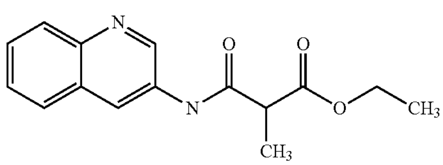 [SMILES: CCOC(=O)C(C)C(=O)Nc1cnc2ccccc2c1] | ethyl 2-methyl-3-oxo-3-(quinolin-3-ylamino)propanoate |
| 7 | 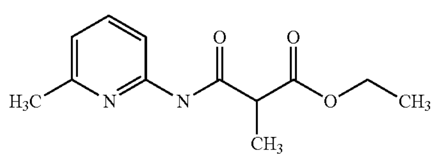 [SMILES: CCOC(=O)C(C)C(=O)Nc1cccc(C)n1] | ethyl 2-methyl-3-[(6-methylpyridin-2-yl)amino]-3-oxopropanoate |
| 8 | 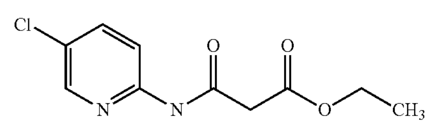 [SMILES: CCOC(=O)CC(=O)Nc1ccc(Cl)cn1] | ethyl 3-[(5-chloropyridin-2-yl)amino]-3-oxopropanoate |

TABLE 2

| No. | IUPAC Name | AIMP2-DX2 Activity in A549 cells | AIMP2-DX2 Activity in H460 cells |
|---|---|---|---|
| 1 | ethyl 3-[(5-chloropyridin-2-yl)amino]-2-methyl-3-oxopropanoate | 5295 | 7668 |
| 2 | ethyl 3-[(6-methylpyridin-2-yl)amino]-3-oxopropanoate | 8070 | 7740 |
| 3 | ethyl 3-oxo-3-(quinolin-3-ylamino)propanoate | 17967 | 5447 |
| 4 | ethyl 3-[(3,6-dimethylpyridin-2-yl)amino]-3-oxopropanoate | 18252 | 4914 |
| 5 | ethyl 3-[(4-hydroxypyridin-2-yl)amino]-3-oxopropanoate | 5721 | 4984 |
| 6 | ethyl 2-methyl-3-oxo-3-(quinolin-3-ylamino)propanoate | 6011 | 5083 |
| 7 | ethyl 2-methyl-3-[(6-methylpyridin-2-yl)amino]-3-oxopropanoate | 6568 | 6082 |
| 8 | ethyl 3-[(5-chloropyridin-2-yl)amino]-3-oxopropanoate | 8045 | 6348 |
| P.C | 4-[(3-ethoxy-1,3-dioxopropyl)amino]-benzoic acid (Example 1) | 11651 | 5012 |
| N.C | DMSO administered | 20089 | 8627 |

What is claimed is:

1. An aminopyridine compound represented by Formula 1, or a pharmaceutically acceptable salt thereof:

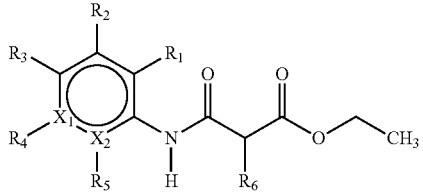

[Formula 1]

wherein:
- $X_1$ and $X_2$ are each independently selected from the group consisting of carbon and nitrogen, wherein both $X_1$ and $X_2$ are not either carbon or nitrogen simultaneously;
- $R_1$ to $R_5$ are each independently selected from the group consisting of a hydrogen, a straight, a branched, or cyclo alkyl of C1-C4, a halogen, and a hydroxyl, wherein all of $R_1$ to $R_5$ are not hydrogen simultaneously; and
- $R_6$ is a hydrogen or an alkyl of C1-C6.

2. The aminopyridine compound or a pharmaceutically acceptable salt thereof of claim 1, wherein the aminopyridine compound represented by Formula 1 is selected from the group consisting of:
- ethyl 3-[(5-chloropyridin-2-yl)amino]-2-methyl-3-oxopropanoate;
- ethyl 3-[(6-methylpyridin-2-yl)amino]-3-oxopropanoate;
- ethyl 3-[(3,6-dimethylpyridin-2-yl)amino]-3-oxopropanoate;
- ethyl 3-[(4-hydroxypyridin-2-yl)amino]-3-oxopropanoate;
- ethyl 2-methyl-3-[(6-methylpyridin-2-yl)amino]-3-oxopropanoate; and
- ethyl 3-[(5-chloropyridin-2-yl)amino]-3-oxopropanoate.

3. A pharmaceutical composition for treating a lung cancer comprising an aminopyridine compound represented by Formula 1 or a pharmaceutically acceptable salt thereof:

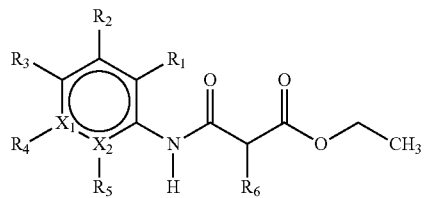

[Formula 1]

wherein:
- $X_1$ and $X_2$ are each independently selected from the group consisting of carbon and nitrogen, wherein both $X_1$ and $X_2$ are not either carbon or nitrogen simultaneously;
- $R_1$ to $R_5$ are each independently selected from the group consisting of a hydrogen, a straight, a branched, or cyclo alkyl of C1-C4, a halogen, and a hydroxyl, wherein all of $R_1$ to $R_5$ are not hydrogen simultaneously; and
- $R_6$ is a hydrogen or an alkyl of C1-C6.

4. The pharmaceutical composition of claim 3, wherein the aminopyridine compound represented by Formula 1 is selected from the group consisting of:
- ethyl 3-[(5-chloropyridin-2-yl)amino]-2-methyl-3-oxopropanoate;
- ethyl 3-[(6-methylpyridin-2-yl)amino]-3-oxopropanoate;
- ethyl 3-[(3,6-dimethylpyridin-2-yl)amino]-3-oxopropanoate;
- ethyl 3-[(4-hydroxypyridin-2-yl)amino]-3-oxopropanoate;
- ethyl 2-methyl-3-[(6-methylpyridin-2-yl)amino]-3-oxopropanoate; and
- ethyl 3-[(5-chloropyridin-2-yl)amino]-3-oxopropanoate.

5. A method for treating lung cancer, the method comprising a step of administering an effective amount of a compound to a subject in need thereof, the compound comprising the aminopyridine compound of claim 1.

* * * * *